United States Patent
Takagi et al.

(10) Patent No.: US 6,921,662 B2
(45) Date of Patent: Jul. 26, 2005

(54) CELL/TISSUE CULTURE APPARATUS

(75) Inventors: Takao Takagi, Shimizu-ken (JP); Setsuo Watanabe, Shizuoka-ken (JP)

(73) Assignee: Takagi Industrial Co., Ltd., Shizuoka-ken (JP)

( * ) Notice: Subject to any disclaimer, the term of this patent is extended or adjusted under 35 U.S.C. 154(b) by 32 days.

(21) Appl. No.: 10/475,552

(22) PCT Filed: Feb. 22, 2002

(86) PCT No.: PCT/JP02/01593
§ 371 (c)(1),
(2), (4) Date: Oct. 22, 2003

(87) PCT Pub. No.: WO02/090490
PCT Pub. Date: Nov. 14, 2002

(65) Prior Publication Data
US 2004/0077072 A1 Apr. 22, 2004

(30) Foreign Application Priority Data
Apr. 24, 2001 (JP) ........................................ 2001-126543

(51) Int. Cl.[7] .............................................. C12M 1/12
(52) U.S. Cl. .............................. 435/297.2; 435/297.4; 435/298.1; 435/299.1
(58) Field of Search .......................... 435/286.5, 298.1, 435/299.1, 297.2, 297.4

(56) References Cited

U.S. PATENT DOCUMENTS 6,121,042 A    9/2000   Peterson et al.

FOREIGN PATENT DOCUMENTS

| | | |
|---|---|---|
| EP | 1078982 | 2/2001 |
| JP | 09313166 | 12/1997 |
| JP | 11504216 | 4/1999 |
| JP | 11514869 | 12/1999 |
| JP | 2001504697 | 4/2001 |
| JP | 2001128660 | 5/2001 |
| WO | WO-9634090 | 10/1996 |
| WO | WO-9713849 | 4/1997 |
| WO | WO-9822573 | 6/1998 |

OTHER PUBLICATIONS

International Search Report.

Primary Examiner—David A. Redding
(74) Attorney, Agent, or Firm—Connolly Bove Lodge & Hutz LLP

(57) ABSTRACT

The invention provides a cell/tissue culture apparatus for applying a physical stimulation necessary for the proliferation and growth of a cell or tissue to a material to be cultivated serving as a cell or tissue to be cultivated, thereby realizing the culture as desired and protecting the material to be cultivated from contamination of various bacteria and so forth. The cell/tissue culture apparatus comprises a cylindrically formed material to be cultivated (matrix 18), a chamber (culture chamber 8) for accommodating therein the material to be cultivated, a circulation path (first circulation path 32) connected to the material to be cultivated through which a culture fluid is circulated in an inner side of the material to be cultivated, a pump (tube pump 36) for controlling a velocity of the culture fluid, control means (controller 60) and so forth, wherein the culture fluid (30) having different flows is supplied to the inner side and an outer side of the material to be cultivated, thereby applying an optional physical stimulation to the material to be cultivated serving as the cell or tissue to be cultivated, thereby realizing the culture as desired and protecting the material to be cultivated from contamination of various bacteria and so forth.

10 Claims, 11 Drawing Sheets

CELL/TISSUE CULTURE APPARATUS

TECHNICAL FIELD

The invention relates to an apparatus for cultivating a cell or tissue (hereinafter referred to as cell/tissue culture apparatus) for use in the culture of a cell or tissue, and so forth to which a tissue engineering is applied, more particularly relates to a cell/tissue culture apparatus for efficiently realizing a metabolism function of a cell or tissue when performing an in vitro culture of the cell or tissue of a living body such as human body and so forth, and applying a physical stimulation necessary for prolongation, differentiation, and acceleration of a cell to a material to be cultivated.

BACKGROUND ART

There has been conventionally employed a method of performing an in vitro culture of a cell or tissue of a living body such as human body, wherein a temperature, a humidity, a carbon dioxide concentration, an oxygen concentration in an incubator (culture housing) are maintained at proper conditions, and the cell is cultivated in the incubator. The cell or tissue is placed in a culture fluid in a suspending state, and it is fixed to an interior or surface of a gel in which the culture fluid ingredient is contained, thereby proliferating and growing the cell or tissue, or the cell or tissue is transplanted in a material, that is exemplified as a matrix or scaffold, a carrier or a mold and so forth (hereinafter referred to as "matrix"), thereby proliferating and growing the cell or tissue in the matrix.

Meanwhile, it is important to apply a physical stimulation to a cell or tissue to be cultivated in addition to an environment condition such as a temperature, a humidity, a carbon dioxide concentration, an oxygen concentration for proliferating and growing the cell or tissue. Such a physical stimulation is an indispensable constituent for facilitating differentiation and growth of the cell or tissue and for growing the cell or tissue to be rendered closer to that in the living body. For a technology for applying a physical stimulation to the cell or tissue for proliferating and growing the cell or tissue, there are, for example, JP 2001-504697A entitled "Application of shear flow stress to chondrocytes", U.S. Pat. No. 6,121,042 entitled "Apparatus and method for simulating in vivo conditions while seeding and culturing three-dimensional tissue constructs", and so forth.

Although it is necessary to add a dynamic condition such as a physical stimulation to a static condition, a so-called culture environment such as a temperature, a humidity, a carbon dioxide concentration, an oxygen concentration for proliferating and growing the cell or tissue, there is a possibility that the control of the dynamic condition together with the static condition renders a control mode complex, and a factor caused by the invasion of various bacteria, and so forth increases. It is an important challenge to protect a material to be cultivated from contamination of various bacteria.

Accordingly, it is a first object of the invention to provide a cell/tissue culture apparatus capable of realizing a desired culture by applying a physical stimulation, which is necessary for proliferation and growth of the cell or tissue, to a material to be cultivated serving as a cell or tissue to be cultivated.

It is a second object of the invention to provide a cell/tissue culture apparatus for protecting the material to be cultivated from contamination of various bacteria and so forth.

DISCLOSURE OF THE INVENTION

To achieve the first object of the invention, a cell/tissue culture apparatus of the invention is characterized in comprising a cylindrically formed material to be cultivated (matrix 18), a chamber (culture chamber 8) for accommodating therein the material to be cultivated, and a circulation path (first circulation path 32) connected to the material to be cultivated through which a culture fluid is circulated in an inner side of the material to be cultivated.

With the cell/tissue culture apparatus having such a configuration, the culture fluid is supplied to the interior of the cylindrical material to be cultivated accommodated in the chamber through the circulation path. Owing to the flow of the culture fluid, a necessary nutrition is supplied to the material to be cultivated through the interior thereof, and also a sheer stress corresponding to the flow of the culture fluid is applied to the material to be cultivated through the interior thereof as a physical stimulation, thereby facilitating the growth of cell or tissue of the material to be cultivated. The physical stimulation mimics a physical stimulation applied to a specific part of a human body, thereby forming a cell or tissue of, e.g., a blood vessel.

A cell/tissue culture apparatus of the invention is characterized in comprising a cylindrically formed material to be cultivated (matrix 18), a chamber (culture chamber 8) for accommodating therein the material to be cultivated, supply means (third circulation path 54) for supplying a culture fluid to the chamber or circulating the same in the chamber, and a circulation path (first circulation path 32) connected to the material to be cultivated accommodated in the chamber through which the culture fluid is circulated in an inner side of the material to be cultivated.

With the cell/tissue culture apparatus having such a configuration, the material to be cultivated is accommodated in the chamber and the culture fluid is supplied or circulated from the supply means. In this case, the supply means supplies the culture fluid successively to the chamber or it circulates the culture fluid between the chamber and a storage tank of the culture fluid. Further, the culture fluid flows to the inner side of the material to be cultivated through the circulation path, and it is supplied to the outer side of the material to be cultivated from the supply means. The sheer stress serving as a physical stimulation is applied to the inner and outer surfaces of the material to be cultivated through the flow of the culture fluid together with the supply of a necessary nutrition. That is, although the sheer stress is applied to the inner and outer surface layers of the material to be cultivated corresponding to the flow of the culture fluid, since the material to be cultivated is cylindrical, the flow of the culture fluid is restricted to one direction, at the inner surface layer of the material to be cultivated, and the sheer stress corresponding to such a flow is applied to the inner side of the material to be cultivated, thereby facilitating the growth of the cell or tissue. That is, according to the physical stimulation through the flow of the culture fluid, it can mimic a physical stimulation applied to a specific part of the human body, thereby forming the cell or tissue, e.g., of a blood vessel.

A cell/tissue culture apparatus of the invention is characterized in comprising a cylindrically formed material to be cultivated (matrix 18), a chamber (culture chamber 8) for accommodating therein the material to be cultivated, a first circulation path (first circulation path 32) connected to the material to be cultivated through which a culture fluid 30 is circulated in an inner side of the material to be cultivated, and a second circulation path (bypasses 40, 42) through which the culture fluid 30 is circulated in an outer side of the material to be cultivated.

With the cell/tissue culture apparatus having such a configuration, since the first and second circulation paths are arranged such that the first circulation path supplies the culture fluid to the inner side of the material to be cultivated and the second circulation path supplies the culture fluid to the outer side of the material to be cultivated, they may be configured independently from each other or may branch off from a common circulation path. In this case, the culture fluid flowing from the first circulation path is restricted in flow to a certain direction by the cylindrical material to be cultivated while the culture fluid flowing from the second circulation path to the interior of the chamber is not fixed in direction. The sheer stress corresponding to the difference in flow is applied to both the inner and outer surface layers of the material to be cultivated owing to such a flow of culture fluid which is configured different in two-flow system, thereby facilitating the growth of cell or tissue of the material to be cultivated. The physical stimulation caused by the culture fluid having different fluid flows can mimic a physical stimulation to be applied to a specific part of the human body.

Since the second circulation path side is opened to the interior of the chamber according to the first and second circulation paths which branch off from a common circulation path, if a fresh culture fluid is supplied from the supply means to the interior of the chamber, the fresh culture fluid is taken into the first circulation path side through the second circulation path, so that nutrition and so forth necessary for culture is supplied to the material to be cultivated together with the physical stimulation, thereby facilitating metabolism of the material to be cultivated. In the case where the first and second circulation paths are independently configured, even if a fresh culture fluid is supplied to the first or second circulation path, or it is replaced with another culture fluid, the same operation can be effected.

The cell/tissue culture apparatus of the invention is characterized in that the second circulation path is bypasses (40, 42) which are formed by allowing the second the second circulation path to branch off from the first circulation path. That is, with the cell/tissue culture apparatus having such a configuration, the culture fluid is forced to flow to the inner side of the material to be cultivated in the chamber through the first circulation path while it is supplied to the outer side of the material to be cultivated through the bypasses. As a result, the sheer stress serving as a physical stimulation through the flow of the culture fluid is applied to the inner and outer surfaces of the material to be cultivated together with necessary nutrition. In this case, the culture fluid flowing from the circulation path is restricted to a certain direction in its flow owing to the cylindrical material to be cultivated while the culture fluid flowing from the bypasses to the interior of the chamber is not fixed in direction. The sheer stress corresponding to the difference in fluid flow is applied to the inner and outer surface layers of the material to be cultivated owing to such a flow of culture fluid which is configured different in two-flow system, thereby facilitating the growth of cell or tissue.

Meanwhile, a small amount of cell is attached to a matrix serving as a material to be cultivated at the early stage of the culture, and hence the attachment of a material (i.e., a so-called an extracellular matrix) produced by the cell is small. The matrix serving as the material to be cultivated is formed of, e.g., spongy or cloth-shaped, wherein a culture fluid flows freely from the inner side of a wall surface of the matrix serving as the cylindrical material to be cultivated to the outer side thereof or from the outer side thereof to the inner side thereof in such a spongy state. However, since gaps in the matrix are filled with extracellular matrix after the middle stage of the culture where the cell is increased to form a tissue, the flow of the culture fluid between the wall surfaces of the cylindrical material to be cultivated is restricted. At this time, since it is difficult to allow a fresh culture fluid to flow to the inner surface side of the material to be cultivated through the first circulation path alone, a fresh culture fluid has to be supplied from another route.

Accordingly, if the bypasses which branch off from the first circulation path are used, a fresh culture fluid supplied to the interior of the chamber is taken in the bypasses and it can be circulated in the material to be cultivated through the first circulation path so that the fresh culture fluid can be supplied to the material to be cultivated. Further, the problem of the pressure difference between the inner and outer sides of the material to be cultivated can be resolved by the provision of the bypasses, and hence the inner and outer sides of the material to be cultivated can be maintained substantially at the same pressure, thereby obviating the inconvenience caused by the pressure difference.

The cell/tissue culture apparatus of the invention is characterized in that a distribution of the amount of flow of the culture fluid is differentiated between the first circulation path and the bypasses, thereby applying different shear stresses are applied to the outer side and the inner side of the material to be cultivated. That is, the culture fluid flowing from the first circulation path is restricted to a certain direction in flow owing to the cylindrical material to be cultivated while the culture fluid flowing from the bypasses to the interior of the chamber is not fixed in direction, and further, the distribution of the amount of flow of the culture fluid is differentiated, thereby applying the sheer stress corresponding to a velocity of flow and flow rate of the culture fluid to the inner and outer surface layers of the material to be cultivated. For example, it is possible to apply a large sheer stress to the inner side of the material to be cultivated and a very small sheer stress can be applied to the outer side thereof.

The cell/tissue culture apparatus of the invention is characterized in further comprising a pump (tube pump 36) for supplying the culture fluid under pressure which flows to the material to be cultivated under pressure, and the supply state under pressure is variable. That is, the culture fluid needs to be supplied under pressure, and the supply state under pressure can be varied, thereby applying a sheer stress as desired to the material to be cultivated.

The cell/tissue culture apparatus of the invention is characterized in further comprising control means (controller 60) for controlling a pressurized supply force of the pump with an optional pattern. That is, the culture fluid can be supplied under pressure to the circulation path in response to the revolution of the pump, and the supply state under pressure can be controlled in response to the rotary pattern, thereby applying a sheer stress serving as a physical stimulation as desired to the material to be cultivated. Further, the physical stimulation is allowed to be varied.

The cell/tissue culture apparatus of the invention is characterized in further comprising, to achieve the second object, a culture unit in which the chamber is formed is rendered in a hermetically sealed state, and the culture unit is detachable. That is, the material to be cultivated can be moved per unit of culture unit, and the hermetical sealing is made easily so that the material to be cultivated can be protected from contamination of various bacteria and so forth.

The cell/tissue culture apparatus of the invention is characterized in further comprising photographing means (CCD camera 86) for photographing the material to be cultivated in the chamber. That is, the photographing of the material to be cultivated in the chamber and the obtaining of image data supplies important data for the proliferation and growth of the material to be cultivated.

The cell/tissue culture apparatus of the invention is characterized in further comprising the culture unit which is transparent as a part or as a whole and photographing means, wherein the material to be cultivated is accommodated and cultivated in the chamber formed in the culture unit, and the material to be cultivated can be photographed by the photographing means from an outside of the chamber. That is, the material to be cultivated can be photographed from the outside of the chamber without disturbing a culture environment in the chamber, thereby obtaining its image data.

Other objects, features, advantages and so forth of the invention are more clarified from the description of the mode for carrying out the invention and the embodiment as illustrated in the drawings.

BEST MODE FOR CARRYING OUT THE INVENTION

The invention and the mode for carrying out the invention are now described in detail with reference to the embodiment as illustrated in the attached drawings.

Figure 1:
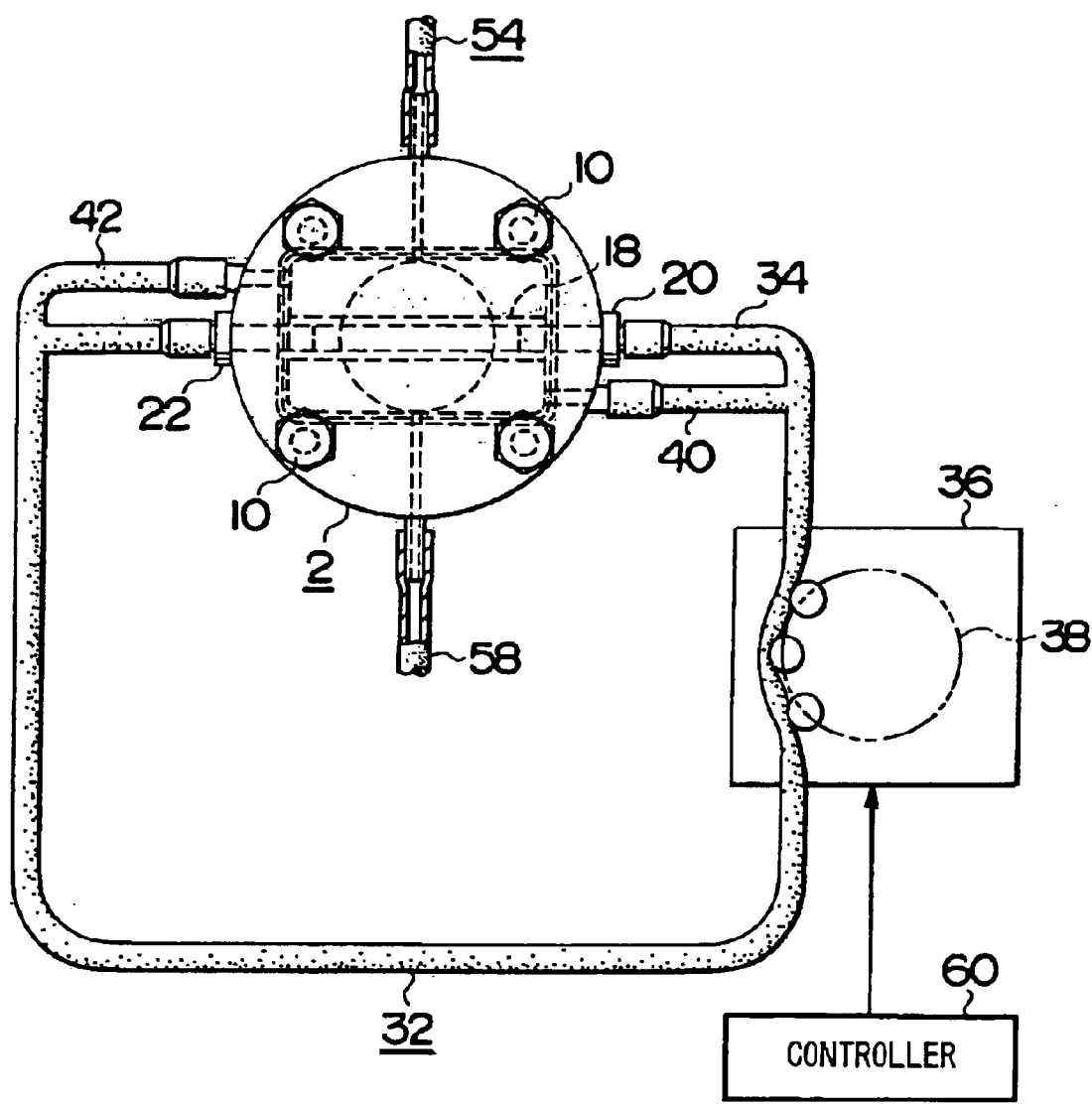
FIG. 1 is a plan view showing a cell/tissue culture apparatus according to an embodiment of the invention.
Figure 2:
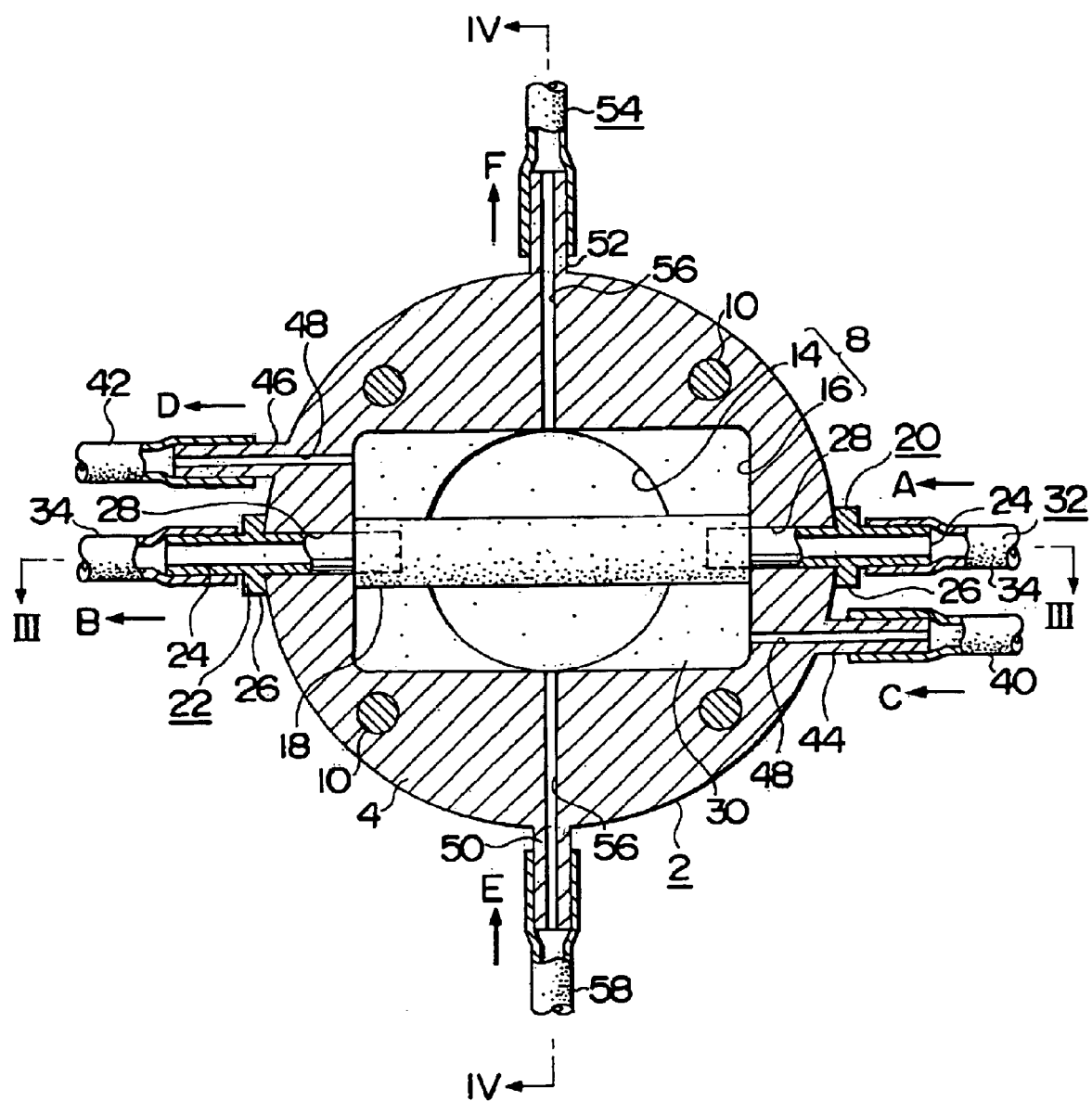
FIG. 2 is a horizontal sectional view showing a culture unit.
Figure 3:
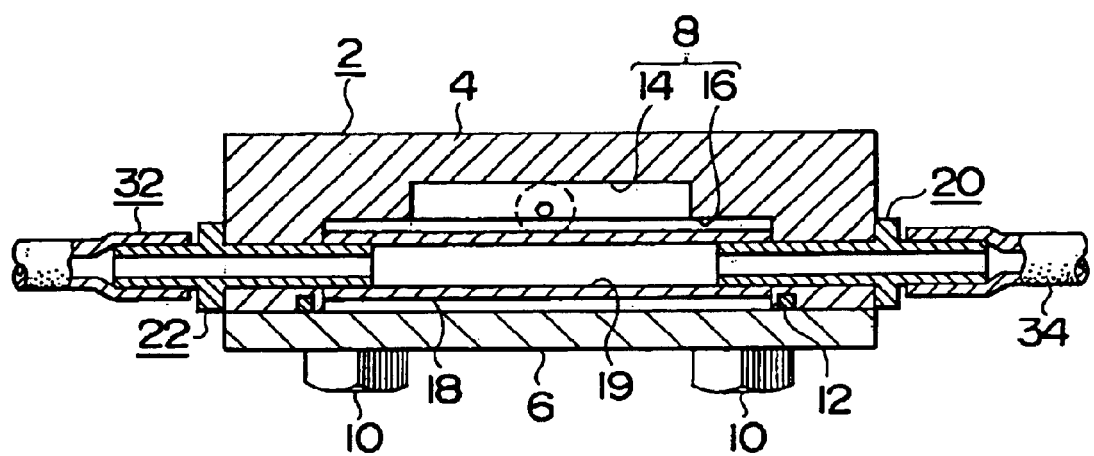
FIG. 3 is a sectional view of the culture unit taken along the line III—III shown in FIG. 2.
Figure 4:
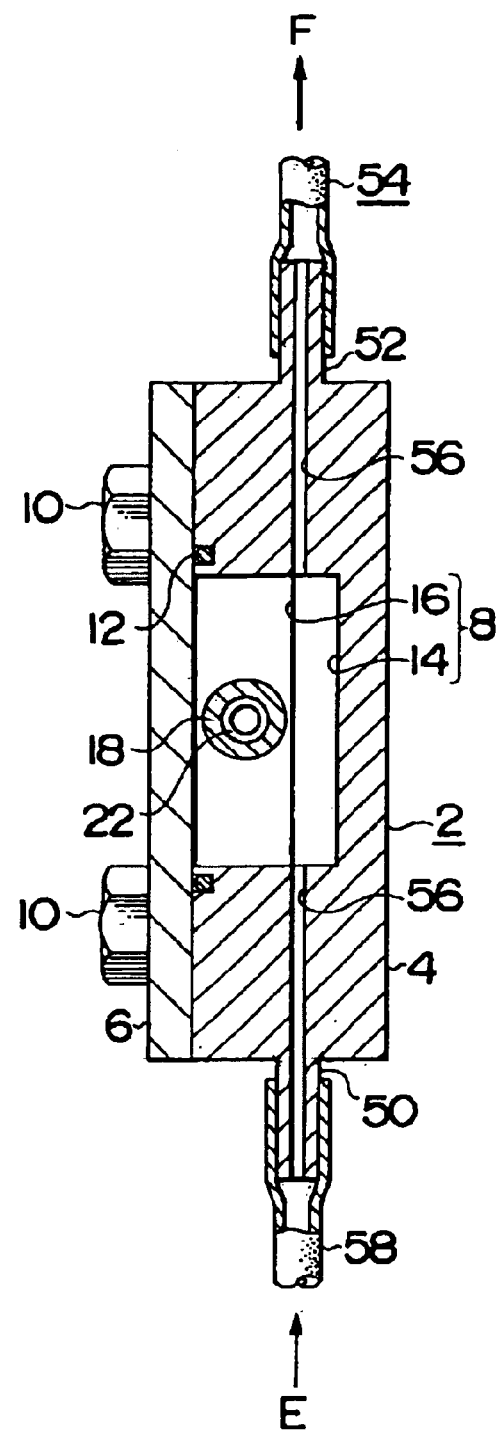
FIG. 4 is a sectional view of the culture unit taken along the line IV—IV shown in FIG. 2.
Figure 5:
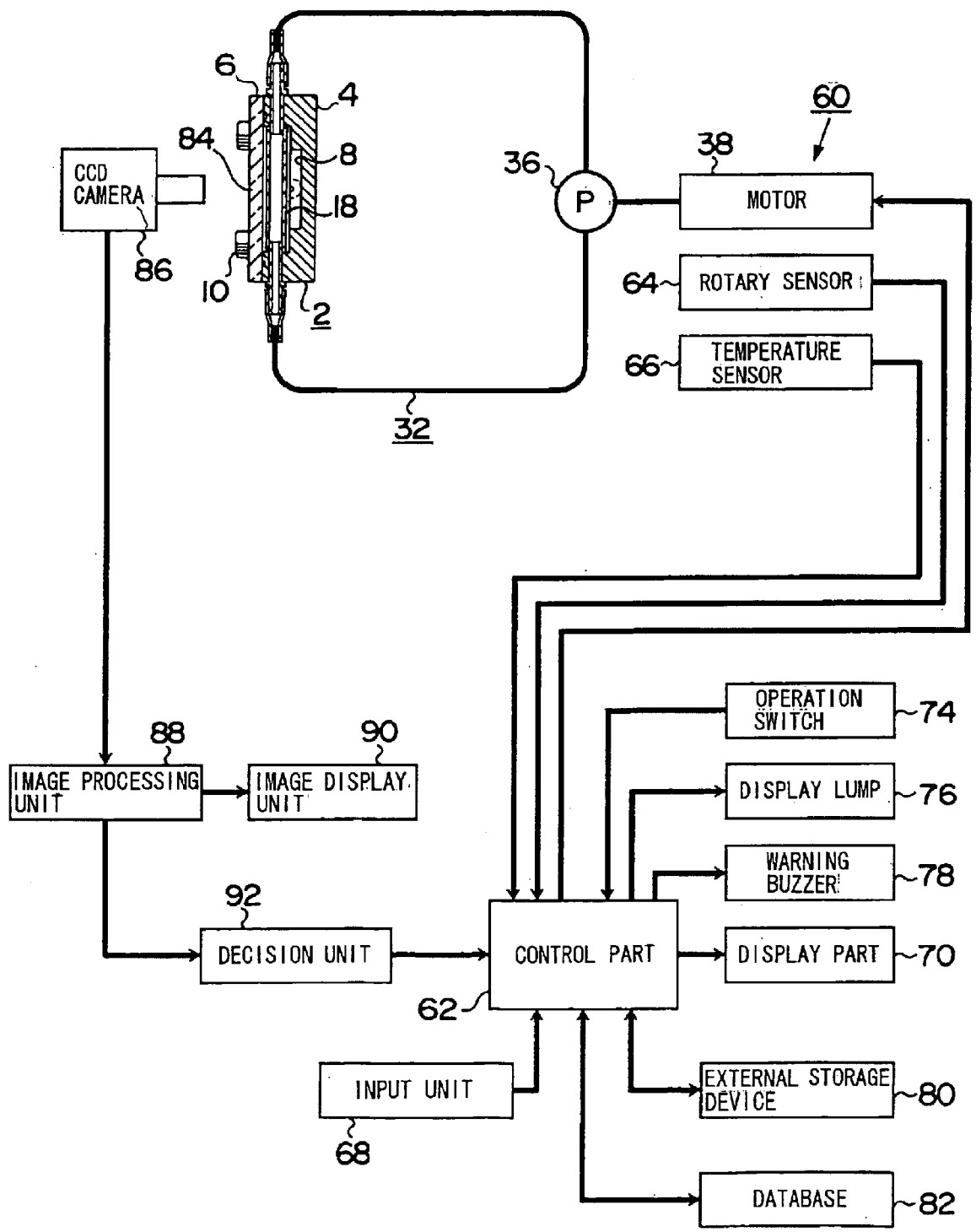
FIG. 5 is a block diagram showing a controller connected to the culture unit.
Figure 6:
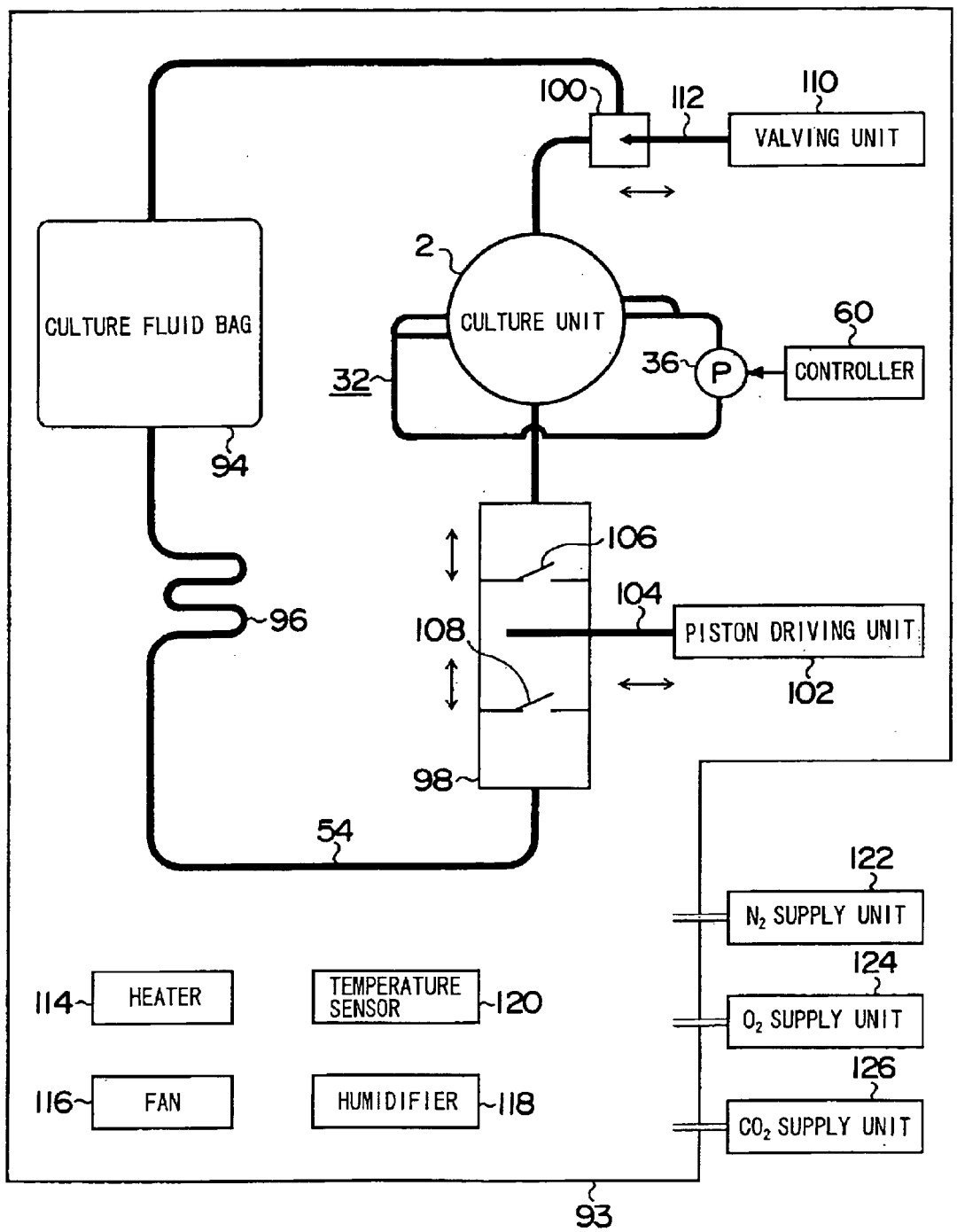
FIG. 6 is a view showing the culture unit installed in a culture housing.

FIGS. 1 to 6 show the cell/tissue culture apparatus according to an embodiment of the invention, wherein FIG. 1 shows a culture unit and so forth on a culture circuit, FIG. 2 shows an internal construction of the culture unit, FIG. 3 is a sectional view of the culture unit taken along the line III—III shown in FIG. 2, FIG. 4 is a sectional view of the culture unit taken along the line IV—IV shown in FIG. 2, FIG. 5 shows the culture circuit and a controller, and FIG. 6 shows the culture circuit and the controller.

A culture unit 2 for cultivating a material to be cultivated serving as a cell or tissue of a living body such as a human and so forth is provided in the cell/tissue culture apparatus, and the culture unit 2 has a high grade heat resistant property and is made up of a synthetic resin material or a metal material from which a material adversely affecting on a living body does not liquate out, for example, fluorine resin, PEEK, high grade heat resistance polypropylene, silicone, stainless steel and so forth.

The culture unit 2 comprises a container 4 and a cover 6 which is detachably attached to the container 4, and a culture chamber 8 serving as a closed culture space is formed in the interior of the culture unit 2. According to the embodiment, the cover 6 is detachably fixed to the container 4 by a plurality of fixing bolts 10, and O rings 12 are interposed between the container 4 and the cover 6, so that a sufficient airtightness is maintained in the culture chamber 8.

The culture chamber 8 comprises a circular portion 14 at an inner side thereof and a rectangular portion 16 at an opening side thereof, and a matrix 18 serving as a cylindrical material to be cultivated is accommodated in the rectangular portion 16 side. That is, the matrix 18 is cylindrical and it is molded as a mold of a blood vessel to be molded as means for proliferating the blood vessel, and the cell of the blood vessel of a human is sowed in the matrix, according to this embodiment.

A pair of culture ports 20, 22 serving as supporting means of the matrix 18 are provided, and they penetrate the rectangular portion 16 of the container 4 from an outer surface side thereof and fixed to the rectangular portion 16 of the container 4. The culture ports 20, 22 project in the culture chamber 8 by a predetermined length and they oppose each other, wherein an opening end of a through hole 19 is engaged with the projecting portion thereof so that the matrix 18 is held at the rectangular portion 16 side of the culture chamber 8. In this embodiment, although the end of the matrix 18 is brought into contact with an inner wall of the culture chamber 8, it can be held in a non-contact state. The culture chamber 8 maybe set to have the shape and size corresponding to the size of the matrix 18 to be cultivated.

According to the embodiment, the culture ports 20, 22 have flanges 26 formed on the midway of a pipe 24, and the pipe 24 penetrates a transparent hole 28 formed in the rectangular portion 16 side of the culture chamber 8 and fixed to the transparent hole 28, and integrated with the culture unit 2. The flanges 26 serve as positioning means for restricting the projecting length of the culture ports 20, 22 relative to the interior of the rectangular portion 16. According to the embodiment, although the culture ports 20, 22 are formed separately from the culture unit 2, they may be integrated with a member constituting the culture unit 2.

A first circulation path 32 through which a culture fluid 30 is circulated in the through hole 19 of the matrix 18 is formed in the culture ports 20, 22, and the first circulation path 32 is made up of a circulation tube 34. A tube pump 36 serving as supply means under pressure of the culture fluid 30 is attached to the first circulation path 32 for facilitating proliferation and growth of the cell or tissue on the matrix 18, and a rotating force is applied to the tube pump 36 by a motor 38 serving as driving means, whereby fluid flow which is the same as the blood flow of a human body is formed by controlling the rotation of the driving means.

Further, according to the embodiment, bypasses 40, 42 serving as the second circulation path through which the culture fluid 30 is circulated outside the matrix 18, i.e. at the outer wall side thereof branch off from the first circulation path 32, and they are connected to bypass ports 44, 46 which are opened to the container 4 of the culture unit 2. The bypass ports 44, 46 project from the outer surface of the container 4 of the culture unit 2, and through holes 48 are formed in the interior of the bypass ports 44, 46. Accordingly, the culture fluid 30 of the first circulation path 32 flows toward the matrix 18 as shown in arrows A, B, and passes through the bypasses 40, 42 and the bypass ports 44, 46 as shown in arrows C, D, then it flows inside the culture chamber 8. Although each tubular diameter of the culture ports 20, 22 and the bypass ports 44, 46 can be set at an optional value, the tubular diameter of the bypass ports 44, 46 side is set to be smaller than that of the culture ports 20, 22 according to the embodiment, so that a flow rate of the culture fluid 30 flowing through the bypass ports 44, 46 is restricteted.

Meanwhile, since the bypasses 40, 42 are opened to the culture chamber 8, the culture fluid 30 supplied to the culture chamber 8 can be taken into the bypasses 40, 42 so that the culture fluid 30 is circulated through the first circulation path 32, thereby circulating the culture fluid 30 in the inner side of the matrix 18. That is, assuming that a fresh culture fluid 30 is supplied to the culture chamber 8, the culture fluid 30 can be circulated through the first circulation path 32 and the matrix 18 through the bypasses 40, 42.

Further, ports 50, 52 for circulation are formed at the circular portion 14 side of the culture chamber 8 in a direction perpendicular to the matrix 18 inside the culture chamber 8, and a third circulation path 54 serving as supply means through which the culture fluid 30 is supplied is formed in the ports 50, 52 for circulation. The ports 50, 52 for circulation project from the outer surface of the container 4 of the culture unit 2, and have through holes 56 therein, and the third circulation path 54 is constituted by circulation tube 58 mounted on the ports 50, 52 for circulation, whereby the fresh culture fluid 30 is supplied from the supply means (e.g., a culture fluid bag 94) of the culture fluid. Depicted by arrows E, F show the culture fluid 30 flowing to the culture chamber 8 through the third circulation path 54 and the flowing direction thereof. That is, although the culture fluid 30 at the first circulation path 32 side is supplied to the inner side of the matrix 18, since the culture fluid 30 at the third circulation path 54 side is supplied to the outer side of the matrix 18 though the culture chamber 8, and to the first circulation path 32 and the inner side of the matrix 18 through the bypasses 40, 42, the fresh culture fluid 30 is constantly circulated in the inner side of the matrix 18.

A controller 60 serving as means for controlling the rotation of the motor 38, monitoring the proliferation and growth of the cell or tissue and so forth is provided in the culture unit 2. The controller 60 has a control part 62 for controlling the rotation of the motor 38 in the manner that a driving current is forced to flow to the motor 38 and so forth, e.g., as shown in FIG. 5, whereby a program control for setting a rotary pattern and so forth is executed by the control part 62. The motor 38 has a rotary sensor 64 for detecting the rotation thereof, and a temperature sensor 66 for detecting a temperature of the motor, wherein each signal for detecting the rotation and the temperature of the motor is supplied to the control part 62 as a control input. The control part 62 has a CPU serving as processing means, a ROM, a RAM, and so forth serving as a memory, and a program such as rotation conditions and so forth is set from an externally connected input unit 68. The control part 62 has a display part 70, an operation switch 74 for giving an operation instruction, operation display means, for example, a display lump 76, a warning buzzer 78 serving as warning means, an external storage device 80 serving as means for storing various data, a database 82, and so forth.

Further, according to the embodiment, a transparent wall portion 84 thorough which the interior of the culture chamber 8 can be seen is provided on a part or the whole of the culture unit 2 at the cover 6 side, and a CCD camera 86 serving as photographing means for photographing the matrix 18 inside the culture chamber 8 is installed in the vicinity of the transparent wall portion 84, wherein image obtained by the CCD camera 86 is supplied to an image processing unit 88 where it is processed, and also a processed image is displayed on an image display unit 90 and is also supplied to a decision unit 92 as decision information. The state of the proliferation and growth of the cell or tissue is decided by the decision unit 92 in response to the change of color, the shape and so forth of the matrix 18 based on the processed image, and the result of decision is supplied to the control part 62. If the state of the matrix 18 in the culture chamber 8 is grasped as image information, and it is observed through this image information, the state of proliferation and growth of the cell or tissue on the matrix 18 and each stage of the growth of the cell or tissue can be visually grasped with accuracy, and an appropriate countermeasure can be taken corresponding to the state of the proliferation and growth of the cell or tissue.

Further, according to the cell/tissue culture apparatus of the invention, it is configured, e.g., as shown in FIG. 6, such that it is accommodated in a culture housing 93 forming an optimum culture environment. The third circulation path 54 has the culture fluid bag 94 for storing the culture fluid 30 therein, a gas absorption tube 96 for allowing the culture fluid circulated through the third circulation path 54 to absorb gas, a fluid supply valve 98 for circulating the culture fluid 30, and a pressure regulating valve 100. A piston 104 which is advanced or retracted by a piston driving unit 102 is provided in the fluid supply valve 98, wherein when the piston 104 is advanced, a valve 106 is opened and a valve 108 is shut while when the piston 104 is retracted, the valve 106 is shut and the valve 108 is opened, thereby effecting delivery of a predetermined amount of culture fluid 30 like the heart. A valve 112 which is advanced or retracted by a valving unit 110 is provided in the pressure regulating valve 100, wherein when the valve 112 is advanced, the pressure regulating valve 100 is shut and when the valve 112 is retracted, the pressure regulating valve 100 is opened, thereby effecting the pressure regulation of the culture fluid 30 in the third circulation path 54.

The culture housing 93 is provided with a heater 114 serving as heating means, a fan 116 serving as blowing means, a humidifier 118 serving as means for setting a humidity as desired, and a temperature sensor 120, and to which $N_2$ is supplied from an $N_2$ supply unit 122, $O_2$ is supplied from an $O_2$ supply unit 124, and $CO_2$ is supplied from a $CO_2$ supply unit 126, thereby forming an optimum culture environment adapted for the proliferation and growth of the cell or tissue.

Figure 7:
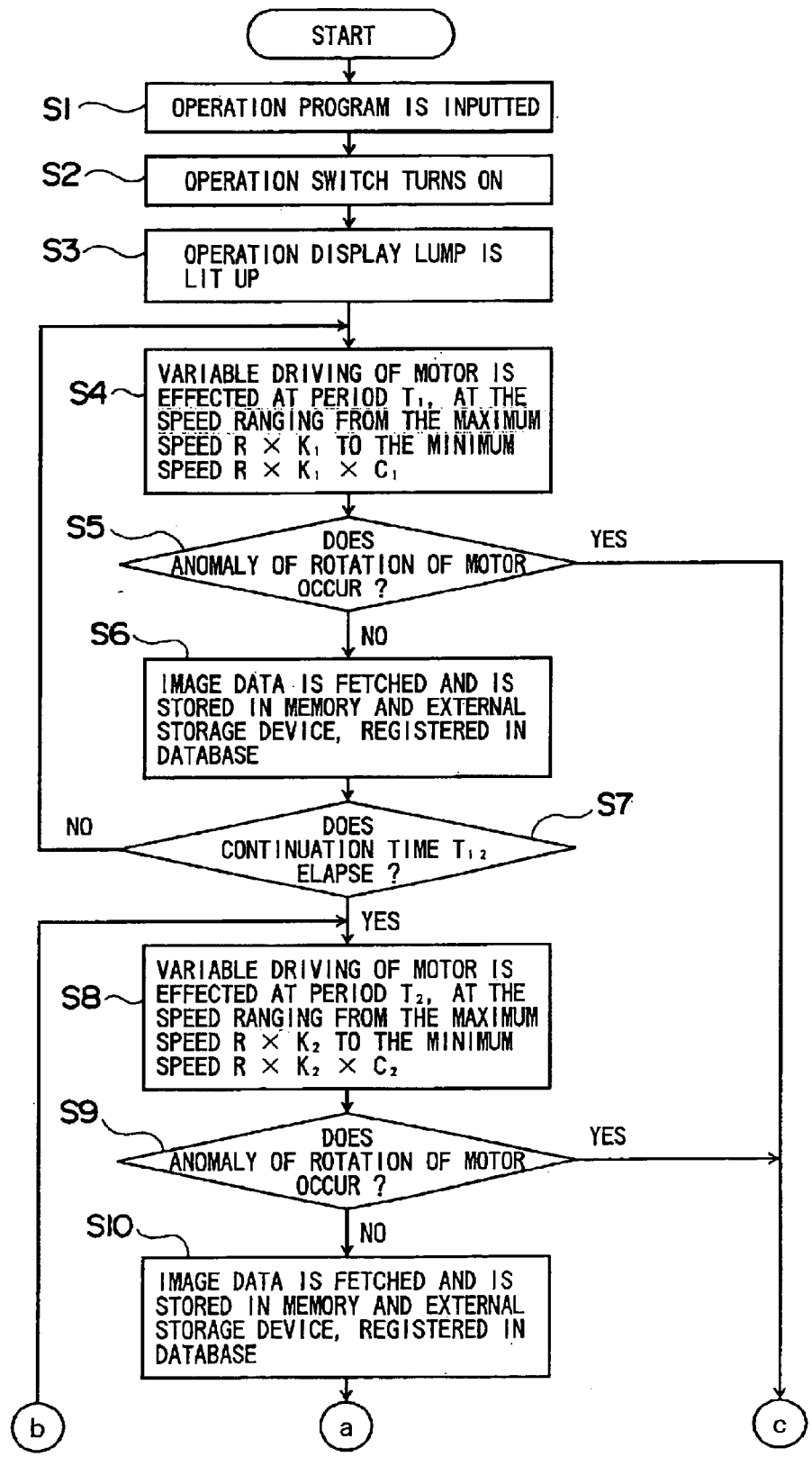
FIG. 7 is a flowchart showing a former half part of a control program.
Figure 8:
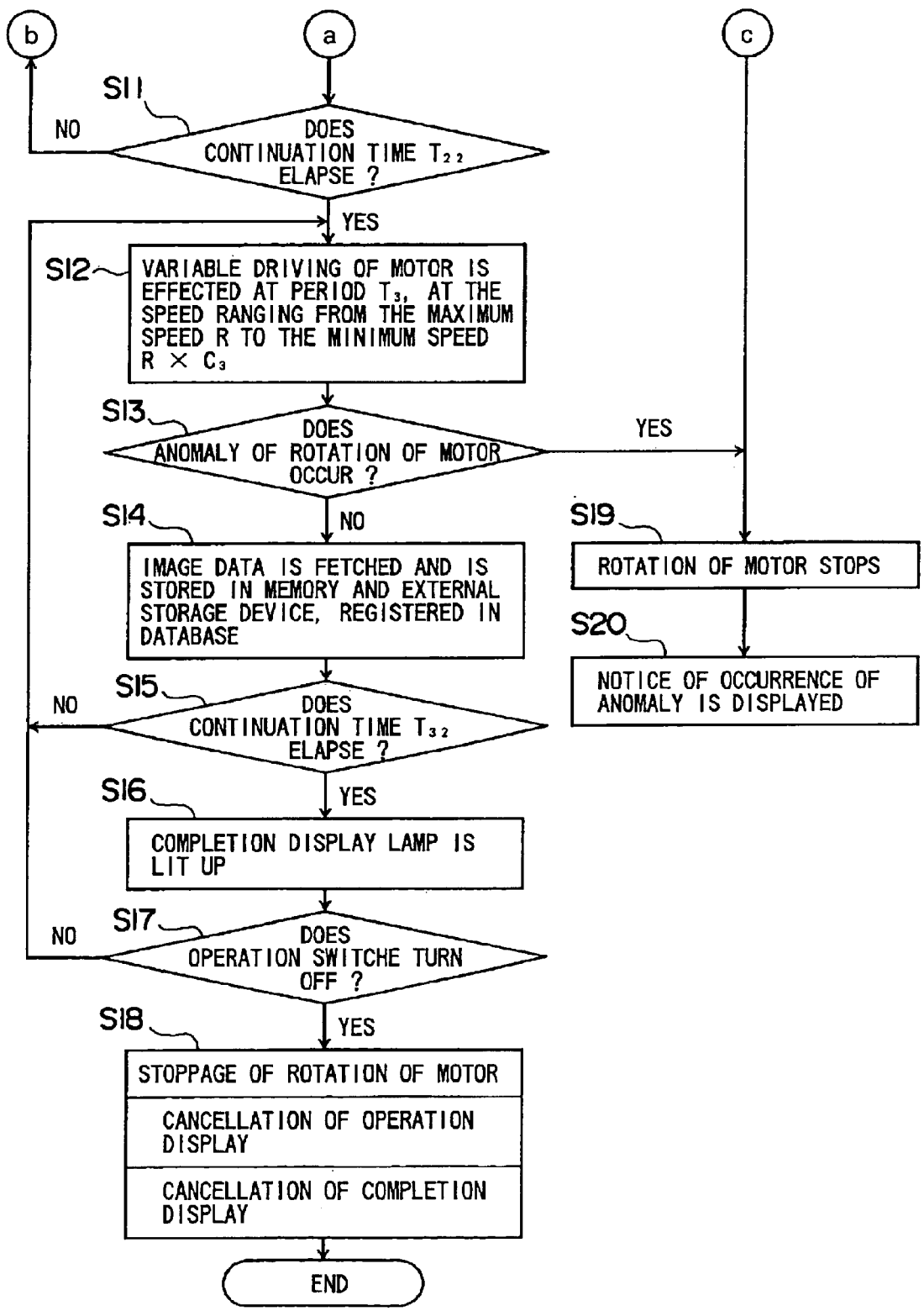
FIG. 8 is a flowchart showing a latter half part of the control program shown in FIG. 7.

A culture processing using the cell/tissue culture apparatus is next described with reference to flowcharts shown in FIG. 7 and FIG. 8. In FIGS. 7 and 8, depicted by circled a, b and c show connecting symbols of the divided flowcharts extending over FIGS. 7 and 8.

In step S1, the controller 60 is set at an operation state, and an operation program is inputted through the input unit 68, thereby setting conditions such as rotary periods $T_1$, $T_2$, $T_3$ of the motor 38 and continuation time $T_{12}$, $T_{22}$, $T_{32}$ and so forth. After setting such conditions, when the operation switch 74 turns ON in step S2, the program goes to step S3 where an operation indication is displayed on the display part 70 and the display lump 76 is lit up.

In step S4, the motor 38 rotates so that variable driving of the motor 38 is effected at period $T_1$, at the speed ranging from the maximum speed $R \times K_1$ to the minimum speed $R \times K_1 \times C_1$, then the program goes to step S5, where during the rotation of the motor, it is decided whether anomaly of the rotation of the motor occurs or not based on detection outputs from the rotary sensor 64 and the temperature sensor 66, and when there dose not occur anomaly, the program goes to step S6. In step S6, image data is fetched from the image processing unit 88, and it is stored in the memory in the control part 62, and the external storage device 80, then it is registered in the database 82.

In step S7, it is decided whether the continuation time $T_{12}$ elapses or not, and the processings of the steps S4 to S6 are continuously executed until the continuation time $T_{12}$ elapses.

Upon elapse of the continuation time $T_{12}$, the program goes to step S8 where the variable driving of the motor 38 is effected at period $T_2$, at the speed ranging from the maximum speed $R \times K_2$ to the minimum speed $R \times K_2 \times C_2$, then the program goes to step S9, where during the rotation of the motor, it is decided whether anomaly of the rotation of the motor occurs or not based on detection outputs from the rotary sensor 64 and the temperature sensor 66 in the same manner as step S5, and when there dose not occur anomaly, the program goes to step S10. In step S10, image data is fetched from the image processing unit 88, and it is stored in the memory in the control part 62, and the external storage device 80, then it is registered in the database 82 in the same manner as step S6.

In step S11, it is decided whether the continuation time $T_{22}$ elapses or not, and the processings of the steps S8 to S10 are continuously executed until continuation time $T_{22}$ elapses.

Upon elapse of the continuation time $T_{22}$, the program goes to step S12 where the variable driving of the motor 38 is effected at period $T_3$, at the speed ranging from the maximum speed R to the minimum speed $R \times C_3$, then the program goes to step S13, where during the rotation of the motor, it is decided whether anomaly of the rotation of the motor occurs or not based on detection outputs from the rotary sensor 64 and the temperature sensor 66 in the same manner as step S9, and when there dose not occur anomaly, the program goes to step S14. In step S14, image data is fetched from the image processing unit 88, and it is stored in the memory in the control part 62, and the external storage device 80, then it is registered in the database 82 in the same manner as step S10.

In step S15, it is decided whether the continuation time $T_{32}$ elapses or not, and the processings of the steps S12 to S14 are continuously executed until the continuation time $T_{32}$ elapses.

Upon elapse of the continuation time $T_{32}$, the program goes to step S16 where a completion display is effected, then the program goes to step S17 where it is decided whether the operation switch 74 turns OFF or not, and the processings of the steps S12 to S16 are executed until the operation switch 74 turns OFF.

When the operation switch 74 turns OFF, the program goes to step S18 where stoppage of the rotation of the motor, and the cancellation of the operation display and completion display are effected, thereby completing the culture program.

In the case where the anomaly of the rotation of the motor is turned out in step S5, step S9, and step S13, the program goes to step S19 where the rotation of the motor stops, then the program goes to step S20 where a notice of generation of anomaly is displayed on the display part 70 as a warning display, and the warning buzzer 78 is sounded.

Figure 9:
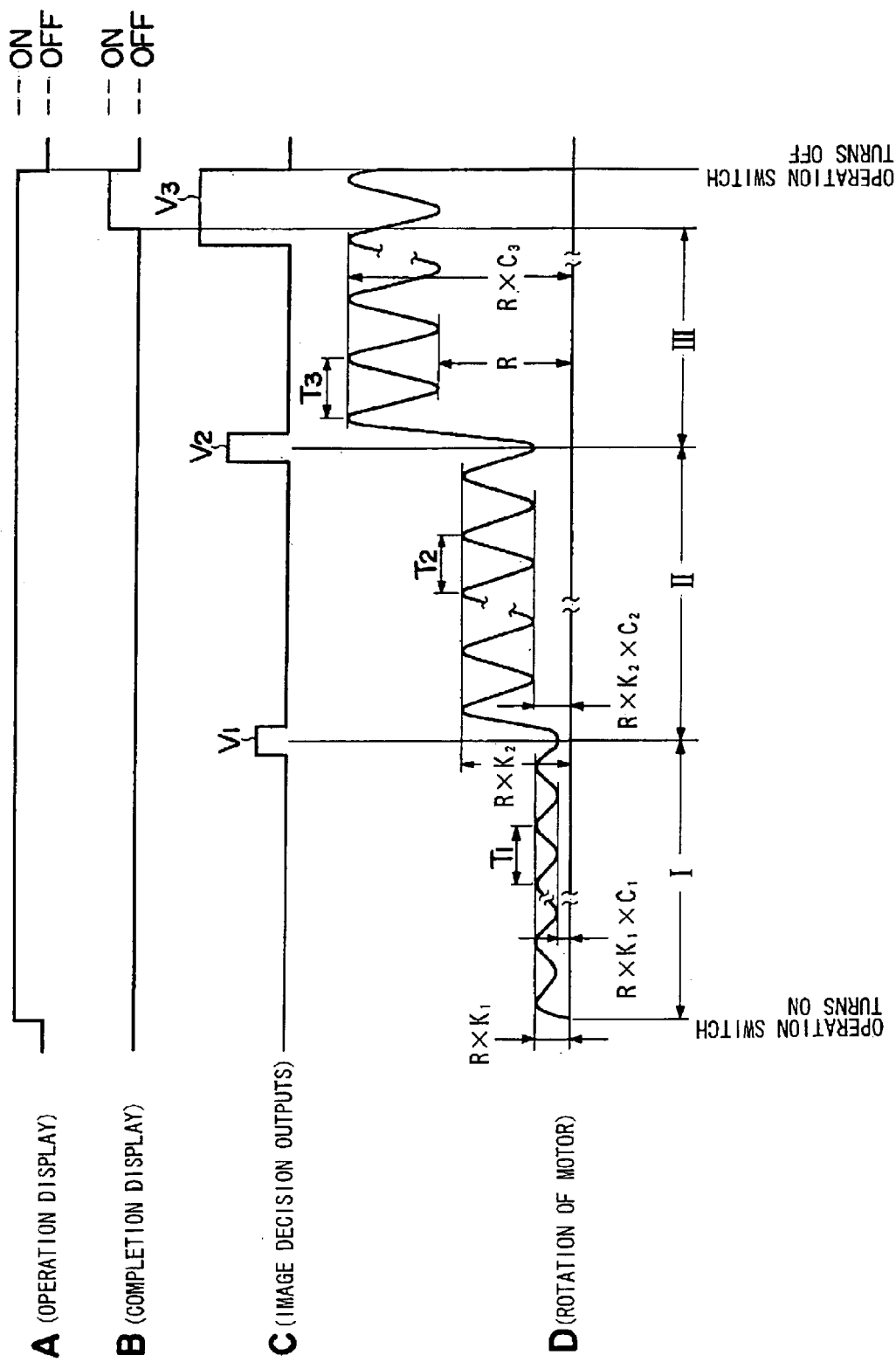
FIG. 9 is a timing chart showing a rotation control operation.

A, B, C and D in FIG. 9 show the operation of the culture program, wherein A shows ON, OFF of the operation display, B shows ON, OFF of the completion display, C shows image decision outputs of $V_1$, $V_2$, $V_3$, D shows a speed of the motor 38, wherein in FIG. 9D, depicted by I indicates a first stage showing the processing in step S4, II indicates a second stage showing the processing in step S8, and III indicates a final stage showing the processing in step S12.

Meanwhile, in this embodiment, the coefficients $K_1$, $K_2$, and $C_1$, $C_2$, $C_3$ used in the processings in step S4, step S8 and step S12 are set values stored in the memory of the control part 62 but they may be changed by inputting them optionally from the input unit 68. Further, according to the embodiment, although it is explained that the circulating direction of the culture fluid 30 is set to one direction, but the direction may be changed to a reverse direction or reciprocal direction.

In the practical culture, the matrix 18 in which the cell or tissue is transplanted is accommodated in the culture chamber 8 after removing the cover 6, and it is installed in the culture housing 93. After a temperature, a humidity, a carbon dioxide concentration, an oxygen concentration and so forth in the culture housing 93 are set to optimum values or conditions, the culture fluid 30 having a flow rate optimum for the cell or tissue is supplied to the matrix 18, thereby executing the culture program.

When the culture fluid 30 is supplied to the matrix 18 through the circulation paths 32, 54, the flow of the culture fluid 30 acts on the inner and outer surfaces of the matrix 18, so that the cell or tissue on the matrix 18 proliferates and grows while it is subjected to the application of a shear stress in the circumferential direction of the culture chamber 8.

Figure 10:
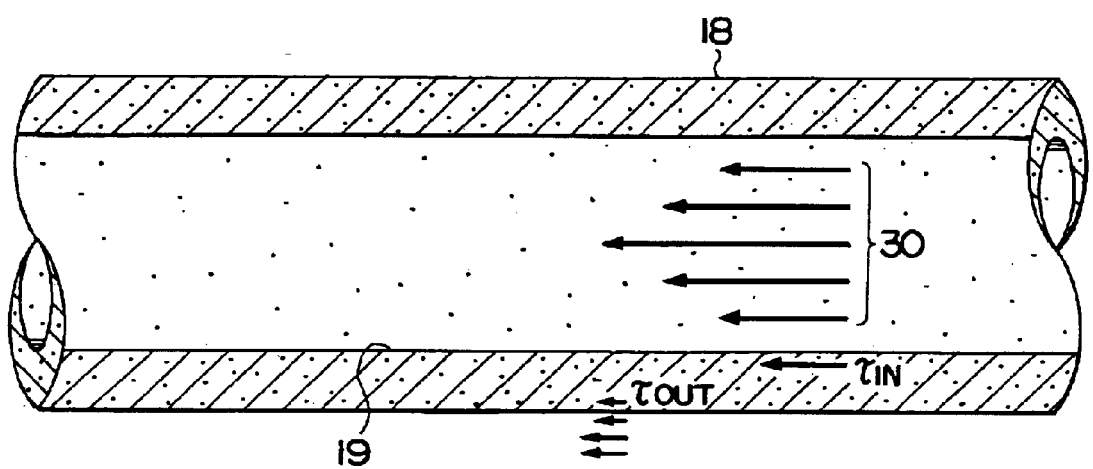
FIG. 10 is a view showing a shear stress generated in a matrix through the flow of the culture fluid.

Described next is the shear stress to be applied to the matrix 18 with reference to FIG. 10. Assuming that a viscosity coefficient of the culture fluid 30 is $\mu$, velocity of flow of the culture fluid 30 is u, variation of the velocity of flow is du, a difference between the different flow velocities is dz, a shear stress τ acting on the surface layer of the matrix 18 serving as a blood vessel is expressed as follows.

$$\tau = \mu \cdot du/dz$$

In this case, the velocity of flow u on the outer wall surface of the matrix 18 is substantially zero, and a shear stress $\tau_{OUT}$ acting on this part is very small, but a large shear stress $\tau_{IN}$ acts on the surface layer of the inner side of the matrix 18. Such a shear stress τ becomes a physical stimulation to contribute to the proliferation and grows of the cell or tissue.

In this case, the shear stress $\tau_{IN}$ acting on the inner side of the matrix 18, i.e., on the inner surface layer of the through hole 19 and the shear stress $\tau_{OUT}$ acting on the inner surface layer of the outer side of the matrix 18 are set in the manner that since the matrix 18 is cylindrical at the inner side of the matrix 18, a flowing direction is restricted, and the velocity of flow of the culture fluid 30 is high and the shear stress $\tau_{IN}$ becomes large while since the velocity of flow of the culture fluid 30 at the outer side of the matrix 18 is slow and has no specific direction, the shear stress $\tau_{OUT}$ is small. As a result, a large shear stress is applied to the inner side of the matrix 18 while a small shear stress is applied to the outer side of the matrix 18. That is, since the cell or tissue which grows in the cylindrical matrix 18 is subjected to an application of a large shear stress at the inner side of the matrix 18 owing to the flow of fluid while it is hardly subjected to an application of a shear stress at the outer side of the matrix 18 owing to the flow of fluid, it grows as a blood vessel inner cuticle tissue at the inner side of the matrix 18 while as a blood vessel outer cuticle tissue at the outer side of the matrix 18. Since the blood vessel tissue of a human is differentiated in inner and outer side thereof, the tissue on the matrix 18 obtained by such culture forms a tissue close to the blood vessel of a living body.

If a flow rate of the culture fluid 30 which is allowed to flow by the tube pump 36 is controlled by a program by which the flow rate is changed to an optimum flow rate as the culture time elapses, a flow of fluid same as that of a living body is obtained. In this case, it is efficient that the flow rate and the velocity of flow of the culture fluid 30 flowing toward the inner side of the matrix 18 is controlled to become an optimum value in response to the stage of growth of the cell to the tissue.

Figure 11:
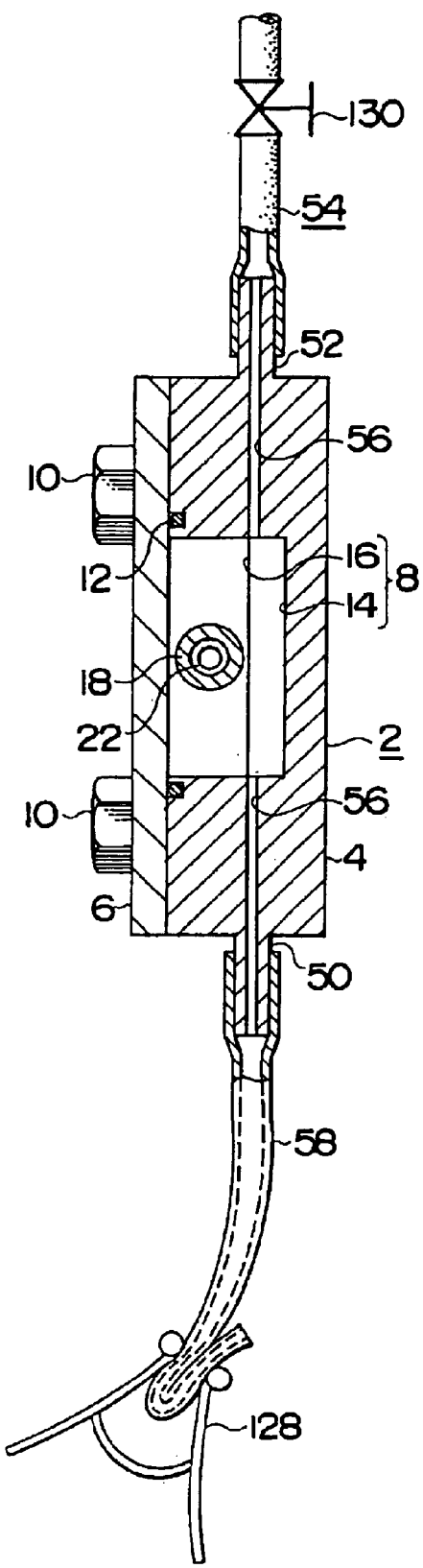
FIG. 11 is a sectional view showing the attachment and detachment of the culture unit.

Upon completion of the execution of the culture program, the culture unit 2 operates such that a circulation tube 58 of the circulation path 54 connected to the ports 50, 52 is shut, for example, as shown in FIG. 11. According to the embodiment, a pinch cock 128, a cock valve 130, which overstride the culture unit 2 and serve as shutting means, are attached to the circulation tube 58, and if the shutting operation is effected, the culture unit 2 can be separated from the circulation path 54 and the culture chamber 8 can be kept in a hermetically sealed state, so that the culture fluid 30 is not leaked out from the culture chamber 8. In this case, the circulation path 32 is separated from the tube pump 36 and the circulation tube 34 is detached from the tube pump 36 and it is better to be moved together with the culture unit 2.

Further, if the culture unit 2 is sterilized by a sterilizing method using an autoclave, and so forth, UV sterilization, gummer rays sterilization, and so forth, the interior of the culture unit 2 can be maintained in an aseptic condition for a long period of time. According to the embodiment, although the pinch cock 128 and the cock valve 130 are employed as means for shutting the circulation tube 58, other closing means may be used.

In this case, the circulation tube 34 at the first circulation path 32 side may be shut by other shutting means as a pinch cock and a cock valve and so forth in the same manner as the circulation tube 58.

Although the bypasses 40, 42 are configured to be formed by branching off from the first circulation path 32 in the embodiment, they may be formed separately independently from the first circulation path 32 as the second circulation path or they may be formed by providing separate openings at side wall portions of the culture ports 20, 22.

In the case where the bypasses 40, 42 are configured as the independent second circulation path, if supply means for supplying a fresh culture fluid is installed at the first circulation path 32 or bypasses 40, 42 sides, the fresh culture fluid together with a physical stimulation such as a necessary shear stress and so forth can be supplied to the inner side of the matrix 18 through the first circulation path 32.

Further, the tube pump 36 has been used as supply means under pressure according to the embodiment, for example, a plunger type pump may be used.

As mentioned in detail above, the following effects can be obtained by the invention.

a It is possible to apply a physical stimulation such as a shear stress caused by the velocity of flow of the culture fluid, and so forth to the material to be cultivated in the chamber in a non-contact state. As a result, it is possible to apply the shear stress, which imitates a physical stimulation on the living body, can be applied to the material to be cultivated, thereby contributing to the facilitation of the culture.

b The manner of flow of the culture fluid is differentiated between the inner side and an outer side of the cylindrical material to be cultivated, and the shear stress can be independently applied to the inner side and outer side of the cylindrical material to be cultivated.

c The culture fluid is supplied to the inner side of the cylindrical material to be cultivated through the first circulation path and it is supplied to the outer side of the cylindrical material to be cultivated through the second circulation path so that the shear stress can be independently applied to the inner side and the outer side of the cylindrical material to be cultivated, and a fresh culture fluid can be supplied from the first circulation path to the material to be cultivated through the second circulation path or bypasses.

d A shear stress corresponding to each stage of the growth of the cell or tissue can be applied to the material to be cultivated through the flow of the culture fluid.

e The culture unit for accommodating therein the material to be cultivated can be moved while it is independently separated from or detachably attached to the culture circuit, thereby protecting the material to be cultivated from contamination of the bacteria and so forth.

f A physical stimulation as desired can be applied to the material to be cultivated, so that a physical stimulation corresponding to the part of a living body can be realized and the facilitation of the culture can be enhanced.

g Each stage of the growth of the cell or tissue can be accurately grasped by image.

Although the configurations, operations and effects of the cell/tissue culture apparatus serving as the mode for carrying out the invention are described with reference to the embodiment as shown in the attached drawings, the invention is not limited to such a mode for carrying out the invention and the embodiment, but it includes all the configurations, which can be predicted or conjectured by a person skilled in the art, such as various configurations, modifications and so forth which can be conjectured by the object, the mode for carrying out the invention, and the embodiment of the invention.

INDUSTRIAL APPLICABILITY

As mentioned above, the cell/tissue culture apparatus of the invention is useful for the culture technology of the cell or tissue to which a tissue engineering is applied, more particularly it is adapted for performing an in vitro culture of the cell or tissue of a living body such as human body, and is also adapted for efficiently realizing a metabolism function of a cell or tissue and applying a physical stimulation necessary for prolongation, differentiation, and acceleration of the cell to the material to be cultivated.

What is claimed is:

1. A cell/tissue culture apparatus comprising:
   a cylindrical material to be cultivated to which a cell to be cultivated is adhered;
   a chamber having a space in which the cylindrical material to be cultivated is accommodated;
   a first port formed in the chamber and connected to the cylindrical material to be cultivated through which the cylindrical material to be cultivated is supported in the space;
   a second port formed in the chamber separately from the first port and communicating with the space;
   a first circulation path connected to the second port through which the culture fluid is supplied to the space so that the culture fluid is circulated in an outer side of the cylindrical material to be cultivated; and a second circulation path connected to the second port through which the culture fluid is supplied in an inner side of the cylindrical material to be cultivated; and supply means under pressure installed in the first circulation path for generating in the culture fluid the same fluid flow velocity as a blood flow.

2. A cell/tissue culture apparatus according to claim 1, further comprising a third circulation path through which the culture fluid is circulated in the space; and gas absorption means for allowing the culture fluid circulated through the third circulation path to absorb nitrogen, oxygen, and carbon dioxide.

3. A cell/tissue culture apparatus according to claim 1, further comprising pressure application means for applying the same pressure to an inner and an outer side of the cylindrical material to be cultivated via the first and the second circulation paths.

4. A cell/tissue culture apparatus according to claim 1, wherein the second circulation path branches off from the first circulation path.

5. A cell/tissue culture apparatus according the claim 4, wherein a distribution of the amount of flow of the culture fluid is differentiated between the first and second circulation paths, thereby applying different shear stresses to the outer side and the inner side of the cylindrical material to be cultivated.

6. A cell/tissue culture apparatus according to claim 1, further comprising a pump for pressurizing and supplying the culture fluid under pressure which flows to the cylindrical material to be cultivated, and the supply state under pressure is variable.

7. A cell/tissue culture apparatus according to claim 6, further comprising control means for controlling a pressurized supply force of the pump with an optional pattern.

8. A cell/tissue culture apparatus according to claim 1, further comprising a culture unit in which the chamber exists in a hermetically sealed state, and the culture unit is detachable.

9. A cell/tissue culture apparatus according to claim 1, further comprising photographing means for photographing the cylindrical material to be cultivated in the chamber.

10. A cell/tissue culture apparatus according to claim 1, further comprising a culture unit which is transparent as a part or as a whole and photographing means, wherein the cylindrical material to be cultivated is accommodated and cultivated in the chamber formed in the culture unit, and the cylindrical material to be cultivated can be photographed by the photographing means from outside of the chamber.

* * * * *

UNITED STATES PATENT AND TRADEMARK OFFICE
CERTIFICATE OF CORRECTION

PATENT NO. : 6,921,662 B2
APPLICATION NO. : 10/475552
DATED : July 26, 2005
INVENTOR(S) : Takao Takagl et al.

It is certified that error appears in the above-identified patent and that said Letters Patent is hereby corrected as shown below:

On the title page item (75), lines 1 & 2, "Shimizu-ken" and "Shizuoka-ken" should read --Fuji-shi--.

Signed and Sealed this

Second Day of January, 2007

JON W. DUDAS
*Director of the United States Patent and Trademark Office*